US008948793B1

(12) United States Patent
Birkhold et al.

(10) Patent No.: US 8,948,793 B1
(45) Date of Patent: Feb. 3, 2015

(54) SYSTEM AND METHOD FOR AUTOMATED REMOTE MESSAGING TO WIRELESS MOBILE DEVICES

(76) Inventors: Bruce R. Birkhold, Scottsdale, AZ (US); Brian Snyder, Phoenix, AZ (US)

( * ) Notice: Subject to any disclaimer, the term of this patent is extended or adjusted under 35 U.S.C. 154(b) by 876 days.

(21) Appl. No.: 13/026,911

(22) Filed: Feb. 14, 2011

Related U.S. Application Data

(60) Provisional application No. 61/303,785, filed on Feb. 12, 2010.

(51) Int. Cl.
*H04W 4/00* (2009.01)

(52) U.S. Cl.
USPC ........ 455/466; 455/412.1; 455/428; 455/461; 455/414.4; 455/417; 455/445; 709/206; 709/238; 709/226; 370/277

(58) Field of Classification Search
CPC . H04L 65/1016; H04L 12/66; H04L 65/1069; H04L 65/40; H04L 29/06176; H04N 21/25866; G06F 15/16; G06F 17/30017; G06F 17/30; H04W 4/16; H04W 24/08; H04W 40/02; H04W 48/18; H04W 4/00; H04W 4/12; H04W 4/14
USPC ........ 455/466, 412.2, 414.4, 417, 412.1, 428, 455/461, 445, 428 OR; 379/38; 709/206, 709/226, 238; 340/539.1; 714/3; 370/277, 370/282
See application file for complete search history.

(56) References Cited

U.S. PATENT DOCUMENTS

| 5,878,212 | A * | 3/1999 | Civanlar et al. ............... 709/203 |
|---|---|---|---|
| 6,680,999 | B1 | 1/2004 | Garcia |
| 6,718,178 | B1 | 4/2004 | Sladek |
| 6,831,563 | B1 | 12/2004 | Contractor |
| 7,388,950 | B2 | 6/2008 | Elsey et al. |
| 2003/0058842 | A1 | 3/2003 | Bud |
| 2003/0088427 | A1 | 5/2003 | Elsey et al. |
| 2004/0039596 | A1 | 2/2004 | Geertsen et al. |
| 2004/0176081 | A1 * | 9/2004 | Bryham et al. ............. 455/414.1 |
| 2004/0199649 | A1 * | 10/2004 | Tarnanen et al. ............. 709/230 |
| 2005/0002510 | A1 | 1/2005 | Elsey et al. |
| 2006/0294108 | A1 | 12/2006 | Adelson et al. |
| 2007/0070940 | A1 | 3/2007 | Vander Veen et al. |
| 2007/0073808 | A1 | 3/2007 | Berrey et al. |
| 2007/0123280 | A1 | 5/2007 | McGary et al. |
| 2007/0172050 | A1 | 7/2007 | Weinstein et al. |

(Continued)

FOREIGN PATENT DOCUMENTS

WO    WO2007038142    4/2007

*Primary Examiner* — Fred Casca
(74) *Attorney, Agent, or Firm* — Booth Udall Fuller, PLC

(57) ABSTRACT

A computerized appointment confirmation system for communication with a mobile device comprising a database comprising data regarding an appointment and a server configured to communicate with an MMS server, the MMS server configured to send an MMS message to the mobile device and receive an MMS response message, receive a communication from the MMS server indicating receipt of the MMS response message by the MMS server, communicate with an SMS server if no MMS response message is received from the mobile device within a predetermined time period, the SMS server configured to send an SMS message to the mobile device and receive an SMS response message, update the database to indicate whether confirmation data was received by the MMS or SMS server from the mobile device, and store in the database data indicating whether an MMS response message or SMS response message was received by the mobile device.

27 Claims, 4 Drawing Sheets

(56) References Cited

U.S. PATENT DOCUMENTS

| | | |
|---|---|---|
| 2007/0280431 A1* | 12/2007 | Alpsten et al. ............... 379/38 |
| 2007/0282654 A1 | 12/2007 | Sarkar |
| 2008/0010105 A1 | 1/2008 | Rose |
| 2008/0013705 A1 | 1/2008 | Yoffie et al. |
| 2008/0045182 A1 | 2/2008 | Randall et al. |
| 2008/0045246 A1 | 2/2008 | Murtagh |
| 2008/0062133 A1 | 3/2008 | Wolf |
| 2008/0086455 A1 | 4/2008 | Meisels et al. |
| 2008/0293392 A1 | 11/2008 | Strother |
| 2008/0299999 A1 | 12/2008 | Lockhart et al. |
| 2010/0125478 A1* | 5/2010 | Bisht ............... 705/8 |
| 2010/0151888 A1* | 6/2010 | Baek ............... 455/466 |

* cited by examiner

SYSTEM AND METHOD FOR AUTOMATED REMOTE MESSAGING TO WIRELESS MOBILE DEVICES

CROSS REFERENCE TO RELATED APPLICATIONS

This document claims the benefit of the filing date of U.S. Provisional Patent Application No. 61/303,785, entitled "System and Method for Automated Remote Messaging to Wireless Mobile Devices" to Bruce Birkhold, which was filed on Feb. 12, 2010, the disclosure of which is hereby incorporated entirely by reference herein.

BACKGROUND OF THE INVENTION

1. Field of the Invention

Aspects of this document relate generally to systems and methods of transmitting reminders and informational messages to remote mobile devices.

2. Description of Related Art

The current medical industry standard for appointment reminders, confirmations and general contact with patient is voice contact and relies on either a manual telephone call by office staff or an automated call placed to patients using an automated voice system. The field of dentistry also has a heavy reliance on postcards for patient communications. There are currently a limited number of firms that offer a reminder system for use in medical fields that operate using a voice message via that is backed up voice by an email or text message requesting confirmation. With current systems, many calls are intentionally or unintentionally not answered by the intended recipient which results in a voicemail message being left for the patient. This voicemail then becomes a generic entry in the message cue and since many people are inundated with messages, the informational content of the voicemail may never be received by the patient.

Industry data shows anticipated "no-show" rates of around 20% with unconfirmed ("naked") appointments which results in thousands of dollars in lost revenue for medical offices every month. While conventional reminder systems may reduce the no show rate, the effect of current systems is a reduction to a no-show rate of approximately 10%, which still results in a high level of lost revenue. Additionally, these systems have high expenditures associated with them due to the cost of postcards and staff time required to make telephone calls.

The concept of sending messages or reminders to wireless mobile devices and requesting a response via SMS or MMS is also well established in the art. See, for example, U.S. Patent Application Publication No. 2008/0062133, which is herein incorporated by reference. However, while current systems and methods in the art may allow for automated reminder messages to be sent to a mobile device, these systems lack the ability to determine or track whether or not a particular messaging format is received by the mobile device.

So as to reduce the complexity and length of the Detailed Specification, and to fully establish the state of the art in certain areas of technology, Applicant herein expressly incorporates by reference all of the following materials identified in each numbered paragraph below.

U.S. Patent Application Publication Nos. 2006/0294108, 2006/0098650, 2008/0013705, and 2007/0280431 provide disclosures of automated messaging systems.

U.S. Patent Application Publication Nos. 2003/0058842, 2005/0002510, 2007/0073808, and 2008/0045246 provide disclosures of methods and systems relating to communicating with a mobile device.

Applicants believe that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), Applicants will amend the specification to expressly recite the essential material that is incorporated by reference as allowed by the applicable rules.

SUMMARY

Implementations of a computerized appointment confirmation system for communication with a mobile device may comprise a database comprising data regarding one or more appointments and a server configured to communicate with an MMS server upon creation of an appointment, the MMS server configured to send an MMS message to the mobile device and receive an MMS response message from the mobile device, receive a communication from the MMS server indicating receipt of the MMS response message by the MMS server, communicate with an SMS server if no MMS response message is received from the mobile device within a predetermined time period, the SMS server configured to send an SMS message to the mobile device and receive an SMS response message from the mobile device, update the database to indicate whether confirmation data was received by the MMS or SMS server from the mobile device, and store in the database data indicating whether an MMS message or SMS message was received by the mobile device.

Particular implementations may comprise one or more of the following features. The MMS message may comprise identifying information that is retained in an SMS response message sent by the mobile device and received by the SMS server. The server may be further configured to update the database in response to receipt of the SMS response message by the SMS server to indicate that an MMS message was received by the mobile device. The server may be further configured to poll at least one MMS server at a predetermined time interval for verification of online statue of the at least one MMS server. The server may be further configured to poll at least one SMS server at a predetermined time interval for verification of online status of the at least one SMS server. The server may be further configured to send an email message to the mobile device if an MMS or SMS response message is not received by the MMS or SMS servers within a predetermined time period and store in the database data indicating receipt of an email response message if an email response message is received from the mobile device. The server may be further configured to communicate with the MMS server wherein the MMS server sends a second MMS message to the mobile device if an SMS response is not received by the SMS server within a predetermined time period. The server may be further configured to receive an error message from the SMS server and generate an exception report. The server may be further configured to send a reminder message to the mobile device at a predetermined time prior to the time at which the appointment is scheduled, the reminder message being sent using the same communication method as that which resulted in a prior response message from the mobile device. The server may be further configured to send a message to the mobile device at a predetermined time prior to the time at which the appointment is scheduled, the message being sent using the same communication method as that which resulted in a prior response message from the mobile device and having additional information relating to the appointment. The communication method may be MMS and the additional information may comprise the appointment time, provider contact information, provider address, and an embedded map of a location of the appointment. The communication method may be SMS and the additional information may comprise the appointment time, provider contact information, and provider address. The communication method may be email and the additional information may comprise the appointment time, provider contact information, provider address, and web link to an online map of the provider's location.

Implementations of a computerized appointment confirmation method for communication with a mobile device may comprise storing in a database, using a server, data regarding one or more appointments, communicating, by the server, with an MMS server upon creation of an appointment, the MMS server configured to send an MMS message to the mobile device and receive an MMS response message from the mobile device, receiving, by the server, a communication from the MMS server indicating receipt of the MMS response message by the MMS server, communicating, by the server, with an SMS server if no MMS response message is received from the mobile device within a predetermined time period, the SMS server configured to send an SMS message to the mobile device and receive an SMS response message from the mobile device, updating the database, by the server, to indicate whether confirmation data was received by the MMS or SMS server from the mobile device, and storing in the database, data indicating whether an MMS message or SMS message was received by the mobile device.

Particular implementations may comprise one or more of the following features. The MMS message may comprise identifying information that is retained in an SMS response message sent by the mobile device and received by the SMS server. The method may further comprise updating the database in response to receipt of the SMS response message by the SMS server to indicate that an MMS message was received by the mobile device. The method may further comprise polling at least one MMS server at a predetermined time interval for verification of online status of the at least one MMS server. The method may further comprise polling at least one SMS server at a predetermined time interval for verification of online status of the at least one SMS server. The method may further comprise sending, by the server, an email message to the mobile device if an MMS or SMS response message is not received by the MMS or SMS servers within a predetermined time period and storing in the database, by the server, data indicating receipt of an email response message if an email response message is received from the mobile device. The method may further comprise communicating, by the server, with the MMS server wherein the MMS server sends a second MMS message to the mobile device if an SMS response is not received by the SMS server within a predetermined time period. The method may further comprise receiving, by the server, an error message from the SMS server and generating an exception report. The method may further comprise sending, by the server, a reminder message to the mobile device at a predetermined time prior to the time at which the appointment is scheduled, the reminder message being sent using the same communication method as that which resulted in a prior response message from the mobile device. The method may further comprise sending, by the server, a message to the mobile device at a predetermined time prior to the time at which the appointment is scheduled, the message being send using the same communication method as that which resulted in a prior response message from the mobile device and having additional information relating to the appointment. The communication method may be MMS and the additional information may comprise the appointment time, provider contact information, provider address, and an embedded map of a location of the appointment. The communication method may be SMS and the additional information may comprise the appointment time, provider contact information, and provider address. The communication method may be email and the additional information may comprise the appointment time, provider contact information, provider address, and web link to an online map of the provider's location.

Implementations of a computer readable medium for computerized appointment confirmation utilizing communication with a mobile device, the computer readable medium having program code stored therein that when executed may be configured to store in a database, using a server, data regarding one or more appointments, communicate, by the server, with an MMS server upon creation of an appointment, the MMS server configured to send an MMS message to the mobile device and receive an MMS response message from the mobile device, receive, by the server, a communication from the MMS server indicating receipt of the MMS response message by the MMS server, communicate, by the server, with an SMS server if no MMS response message is received from the mobile device within a predetermined time period, the SMS server configured to send an SMS message to the mobile device and receive an SMS response message from the mobile device, update the database, by the server, to indicate whether confirmation data was received by the MMS or SMS server from the mobile device, and store in the database, data indicating whether an MMS message or SMS message was received by the mobile device.

Particular implementations may comprise one or more of the following features. The MMS message comprises identifying information that is retained in an SMS response message sent by the mobile device and received by the SMS server. The computer readable medium may be further configured to update the database in response to receipt of the SMS response message by the SMS server to indicate that an MMS message was received by the mobile device. The computer readable medium may be further configured to poll at least one MMS server at a predetermined time interval for verification of online status of the at least one MMS server. The computer readable medium may be further configured to poll at least one SMS server at a predetermined time interval for verification of online status of the at least one SMS server. The computer readable medium may be further configured to send, by the server, an email message to the mobile device if an MMS or SMS response message is not received by the MMS or SMS servers within a predetermined time period and store in the database, by the server, data indicating receipt of an email response message if an email response message is received from the mobile device. The computer readable medium may be further configured to communicate, by the server, with the MMS server wherein the MMS server sends a second MMS message to the mobile device if an SMS response is not received by the SMS server within a predetermined time period. The computer readable medium may be further configured to receive, by the server, an error message from the SMS server and generating an exception report. The computer readable medium may be further configured to send, by the server, a reminder message to the mobile device at a predetermined time prior to the time at which the appointment is scheduled, the reminder message being sent using the same communication method as that which resulted in a prior response message from the mobile device. The computer readable medium may be further configured to send, by the server, a message to the mobile device at a predetermined time prior to the time at which the appointment is scheduled, the message being sent using the same communication method as that which resulted in a prior response message from the mobile device and having additional information relating to the appointment. The communication method may be MMS and the additional information may comprise the appointment time, provider contact information, provider address, and an embedded map of a location of the appointment. The communication method may be SMS and the additional information may comprise the appointment time, provider contact information, and provider address. The communication method may be email and the additional information may comprise the appointment time, provider contact information, provider address, and web link to an online map of the provider's location.

Implementations of a computerized appointment confirmation system for communication with a mobile device may comprise a user interface configured to accept user input information, the user input information comprising information relating to an appointment and information relating to a mobile device, a database that stores the information relating to the appointment and the mobile device, and a server configured to determine whether the mobile device is able to receive a message using an MMS or SMS format and if the mobile device is able to receive the message using an MMS or SMS format, store the communication format that is able to be received by the mobile device in the database.

The present invention provides among other things systems and methods of automatically generating appointment confirmation and reminder messages using a web-based cloud computing application and SMS, MMS, voice, and/or email messaging capabilities.

Aspects and applications of the invention presented here are described below in the drawings and detailed description of the invention. Unless specifically noted, it is intended that the words and phrases in the specification be given their plain, ordinary, and accustomed meaning to those of ordinary skill in the applicable arts. The inventors are fully aware that they may be their own lexicographers if desired. The inventors expressly elect, as their own lexicographers, to use only the plain and ordinary meaning of terms in the specification unless clearly stated otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of this disclosure.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. §112, ¶ 6. Thus, the use of the words "function," "means" or "step" in the Detailed Description or Description of the Drawings or claims is not intended to somehow indicate a desire to invoke the special provisions of 35 U.S.C. §112, ¶ 6, to define the invention. To the contrary, if the provisions of 35 U.S.C. §112, ¶ 6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. §112, ¶ 6. Moreover, even if the provisions of 35 U.S.C. §112, ¶ 6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

BRIEF DESCRIPTION OF THE DRAWINGS

Implementations will hereinafter be described in conjunction with the appended drawings, where like designations denote like elements, and.

Figure 1:
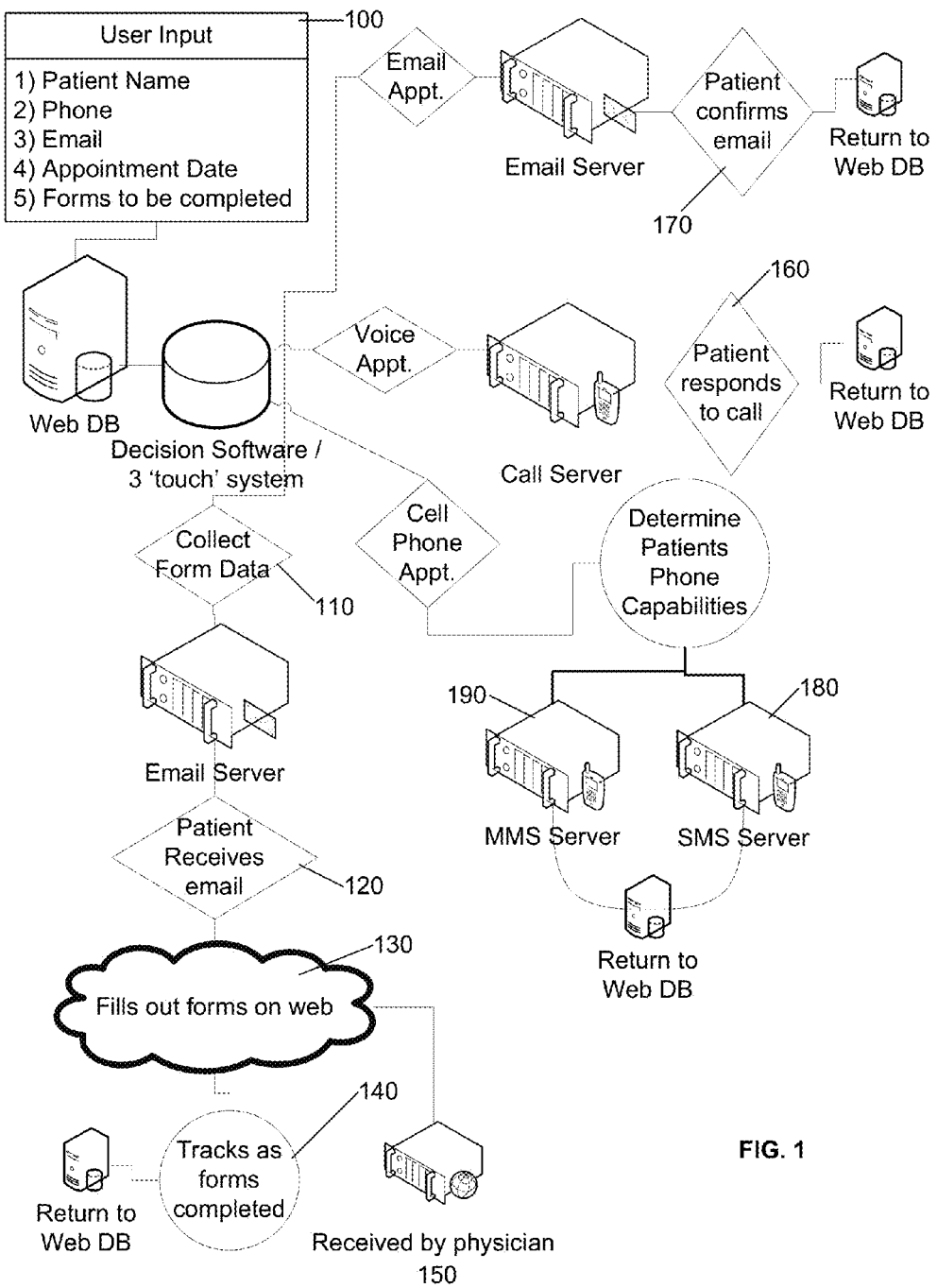
FIG. 1 is a block diagram of a system.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the invention is not limited to the examples that are described below.

An automated patient contact system may be used to accomplish various tasks associated with appointment reminders, confirmations and general contact with patients in the medical, dental, or other industries where client contact is needed and offers the advantage of cost savings due to reduction of staff time, postcards, postage and other supplies related to mailing, and reduction of lost revenue as a result of significantly fewer "no-shows" and patients arriving at times other than their scheduled appointment times than with conventional patient or client contact systems.

Utilizing the wireless cellular communication industry as a medium for conducting patient contact is advantageous because wireless providers tightly monitor solicitors and protect their users from unwanted contacts, in compliance with current U.S. Consumer Best Practices Guidelines for Cross-Carrier Mobile Content Programs, herein incorporated by reference. Wireless providers are easily able to block any solicitor or other entity that contacts wireless subscribers directly and creates user complaints regarding unwanted contacts. This reduces the amount of "spam" or "junkmail" communications that are received via SMS, MMS, and other messaging formats and thus, increases the likelihood that users will read and respond to SMS, MMS, and other text messages that are received as they do not inherently perceive the majority of communications received using these methods to be unsolicited. A potential advantage of the system and methods disclosed herein may be the ease of patient access to last minute information that is needed to allow the client to safely arrive at the appointment on time. For example, using MMS messaging may allow the system to provide the patient with an embedded phone link, map, and any other pertinent information so as to prevent the patient from having to open an email and click a web link to obtain this information while en route to the appointment.

Furthermore, implementations of the system and methods disclosed herein may relate to information pertaining to a patient's medical care although are not limited as such. This may allow for messages to be classified in a manner so as to avoid the regulations of marketing, advertising, and other promotional materials. Patients must "opt-in" to the receiving messages from the automated system and may do so by providing their cellular telephone number to their health care provider or by signing an "opt-in" agreement authorizing the health care provider to contact them using the system and methods of this disclosure. Thus, as the wireless mobile device user has already granted permission to the health care provider to contact the user in this manner, complaints to the wireless carriers regarding unwanted communications are unlikely.

Patients' confidential medical information must be stored electronically using appropriate safeguards to prevent intrusions from outside the system or misappropriation of this sensitive data by software applications installed onto server or other hardware components used to store patient data. Thus, an additional advantage of some implementations of the system and methods disclosed herein is that the application may run remotely and provide a web-based user interface by which users may enter appointment and other sensitive or non-sensitive information, and thus, may operate so as not to provide a gateway of access into the health care provider's main databases system that houses sensitive patient information as the system disclosed herein is capable of running externally to the health care provider's own computer data storage systems.

Furthermore, the Health Insurance Portability and Accountability Act (HIPAA) regulates the type of message that may be carrier in a patent communication and limits content that may be considered to be for marketing purposes rather than for communication relating to the patient's healthcare. Thus, the system and methods disclosed therein may be implemented in such a manner as to provide a closed and untainted channel for conveyance of medical information, however, one of ordinary skill in the art would recognize that the present disclosure is not limited as such. Additionally, HIPAA requires the use of encryption both for data entry on a web-based interface and in transmission over the Internet. Therefore, while one of ordinary skill in the art would realize that while this disclosure is not intended to be limited as such, implementations of this disclosure may include these encryption features.

In an aspect of the invention, a system and method of automatically confirming appointments and generating client contacts to provide reminders and other client communications is accomplished using a cloud-computing or local application that remotely provides a web-based or other interface for user input and generates electronic notifications to communicate with users regarding their appointments or other events by sending one or more messages to the wireless mobile device of a user via SMS, MMS, email voice, or any other messaging format. The system may also handle appointment cancellations by removing any future scheduled patient contact relating to the appointment from the system.

It is to be understood that such a system includes components such as computers, servers, or other devices having a hard disk and a storage controller that may be employed with any form of memory device including all forms of sequential, pseudo-random, and random access storage devices. Storage devices as known within the current art include all forms of random access memory, magnetic and optical tape, magnetic and optical disks, along with various other forms of solid-state mass storage devices. The current invention applies to all forms and manners of memory devices including, but not limited to, storage devices utilizing magnetic, optical, and chemical techniques, or any combination thereof.

Figure 2:
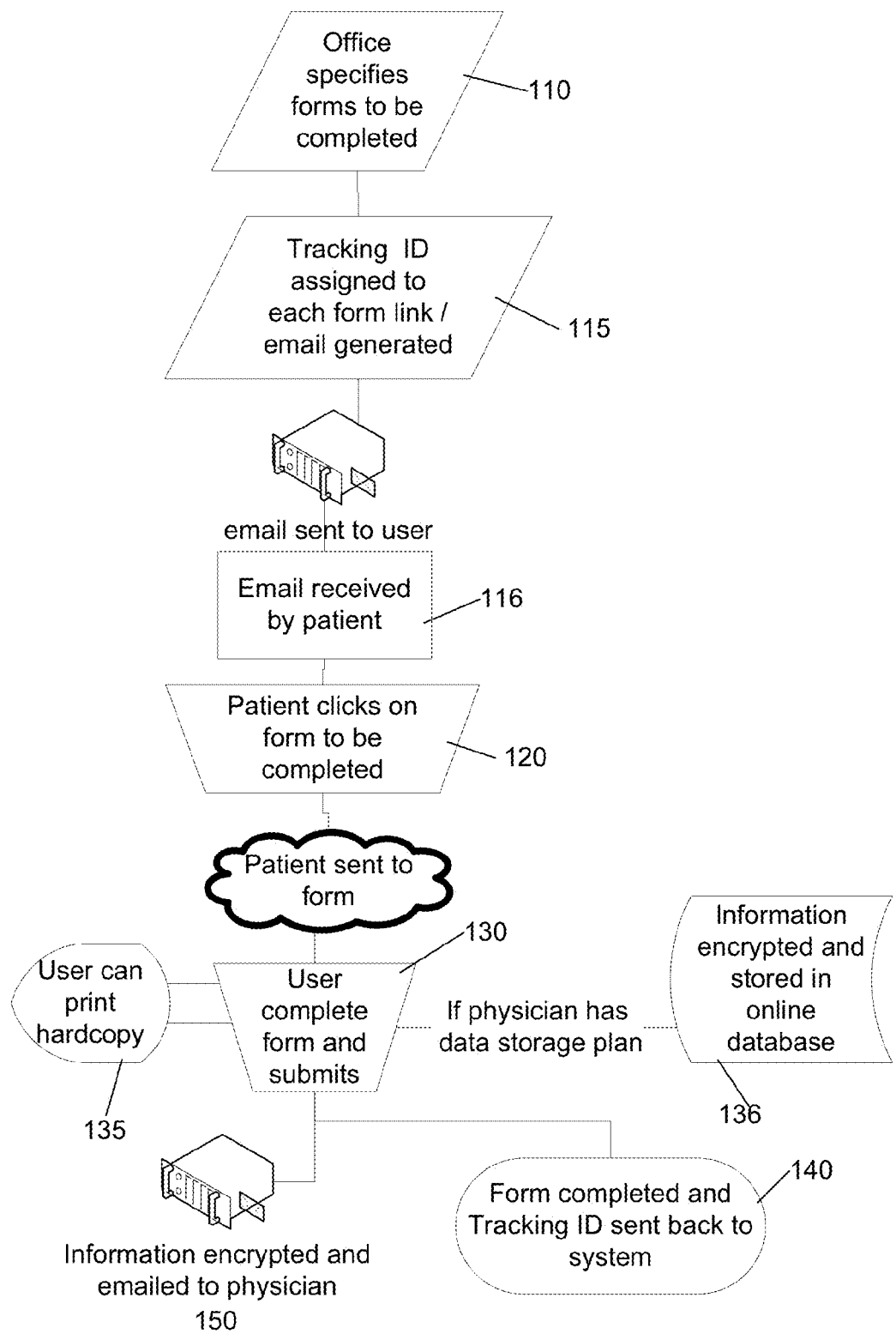
FIG. 2 is a block diagram of a method of using a web-based system to complete user forms.

As shown in FIGS. 1-2, in an aspect of the invention, a user employed by a health care provider or other entity employing the systems disclosed herein enters information that may include, but is not limited to patient name, cellular and/or other telephone numbers, date and time of the appointment, email address, and a preferred communication method into a web-based user interface 100 that is displayed on the screen of the health care provider staff member's computer or other electronic device.

Additionally as shown in FIG. 2, in certain implementations, the staff member may then select from a list of forms which may include predefined groups of forms such as, but not limited to, basic visit forms, new patient forms, office procedure visit forms, etc. 110, which are then sent to the patient's email address 116 or to the patient's mobile device via MMS or SMS messaging. A tracking ID may be assigned to each form link or email generated 115. The forms may be sent directly or a web link may be provided so that the patient may access the needed forms 120 and fill out the forms 130. In some embodiments, an automatic follow-up option may be enabled to send the patient reminder email, MMS, or SMS messages to encourage completion of the forms. The system may track completion of the forms 140 and an embedded link may be sent that allows the patient to access all forms or only the uncompleted, outstanding forms. Additionally, if all forms are not competed by the time of the appointment, the system may allow the patient to access the outstanding forms using a portable computer or other interactive device in the waiting room or other designated area so that the patient may complete the forms on the date of the appointment. While not limited as such, the system may then maintain a digital data entry path thereby eliminating the need for any associated paperwork and may enable data to be transmitted via the Internet using WAN or LAN at the health care provider's office.

Upon patient completion of the designated forms, the tracking ID is sent back to the system 140 and a form completion email may then be sent to the health care provider and the forms may be emailed by the patient to the system in an encrypted format and stored in a database 136 within the system and/or transmitted to the health care provider 150. When forms are returned to the office, they may be in a printable format, such as for example pdf, or they may be in a digital form such as CSV, HL7, or any other format known to those of ordinary skill in the art. Thus, the forms may then be printed 135 and integrated into a paper-based office or migrated digitally into the provider's existing office management or electronic medical records software.

Some implementations may allow for storage of an encrypted copy of patient information on a secured server within the system. The server may be set up to allow only inflow of new encrypted files so that files cannot be retrieved or returned to a readable state without the appropriate decryption key. This may allow patients to submit forms and update their medical information, for example, in response to an automatically generated reminder email, MMS, or SMS message, to reduce the costs associated with data entry of patient information by healthcare providers in maintaining digital medical records.

Some implementations of the system may also provide installation and set-up of encryption and decryption software as well as access to a dedicated email account for receiving completed patient forms and other correspondence. The system may also allow the user to choose a decryption phrase so that the information contained in an unsecured email account will remain encrypted until the decryption phrase is supplied.

Figure 3:
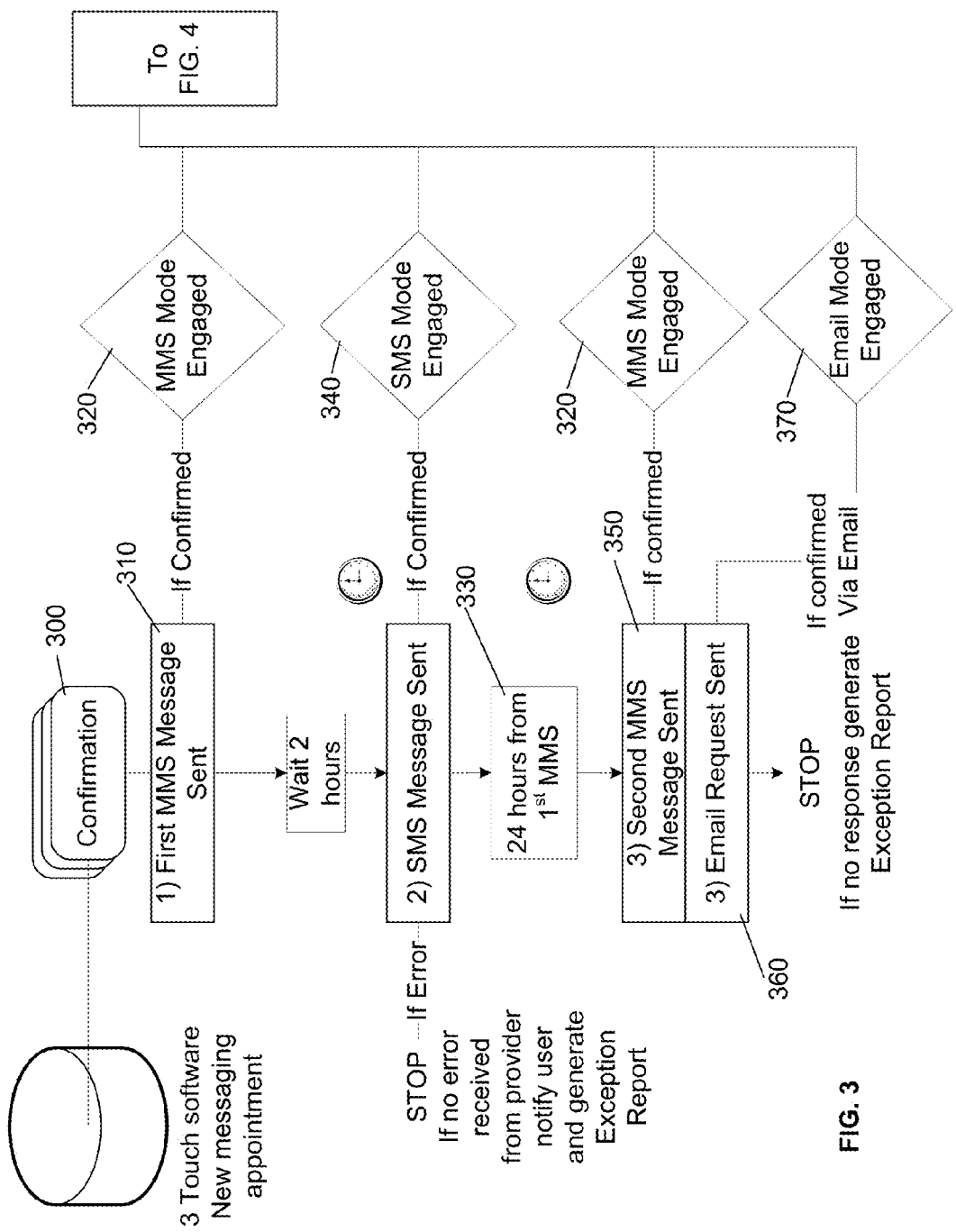
FIGS. 3-4 are block diagrams of a method of transmitting reminder messages to a mobile device.

In some implementations, as shown in FIG. 3, after a new appointment is set, the system initiates a series of multiple touch confirmation and reminder transmissions to the patient. The system may first generate an electronic confirmation message 300 that is sent to the wireless mobile device user who is the subject of the appointment. Initially, this message may be sent in the form of an MMS message 310 and if a response message is received from the mobile device confirming receipt of the initial MMS message, the system may store this information in a database thereby enabling "MMS Mode" 320 which indicates that the mobile device is capable of receiving MMS messages and that future correspondence is to be sent using the MMS message format. If no response message is received after a predetermined time interval, an SMS confirmation message is then sent to the mobile device 330. If a response message is received, the system may store this information in a database thereby enabling "SMS Mode" 340 which indicates that the mobile device is capable of receiving SMS messages and that future correspondence is to be sent using the SMS message format. If no response is received within a predetermined time period after the SMS message is sent, a second MMS confirmation message 350 is sent to the mobile device and if a response is received, the system stores this information in a database thereby enabling "MMS Mode" 320 as described above. Additionally, an email confirmation message may be sent 360 and if a response email is received from the patient, the system may store this information in a database thereby enabling "Email Mode" 370 which indicates that the patient is able to receive email via a mobile device or other computer and that future correspondence is to be sent using email. If no response is received to either the second MMS confirmation message or the email message within a predetermined time period, the server may then generate an exception report. Similarly, an exception report may be generated if an error is received from an MMS or SMS server in response to attempted transmission of an MMS or SMS message which may trigger an automated voice follow-up or other contact to be initiated by the system. The exception report may then be transmitted to the health care provider's office so that a decision may be made as to what, if any, action should be taken (e.g. ignore, make a human voice call, or cancel the appointment, etc.). Additionally, an email may be sent to the patient along with an MMS or SMS message alerting the patient to the fact that an email message has been sent.

A mobile device that is capable of receiving MMS messages may send a response message in either MMS or SMS format. Thus, when an MMS message is sent by the MMS server to the mobile device, if the response message is sent in MMS format, the response message will be sent back to the MMS server and may then be stored in the database within the disclosed system as described above. However, in the instance in which the mobile device sends an SMS response message, this response message is then received by an SMS server 180. Traditionally, this SMS response message does not contain any information that would cause it to be linked to the original MMS message that was sent by the MMS server 190. However, in implementation of the system and methods disclosed herein, the original MMS message contains identifying information that is retained even if the response is sent in SMS format. This information then allows the SMS server 180 to communicate to the system server that an MMS message was received by the mobile device and the mobile device's ability to receive MMS messages may then be stored in the database thereby enabling "MMS Mode."

Figure 4:
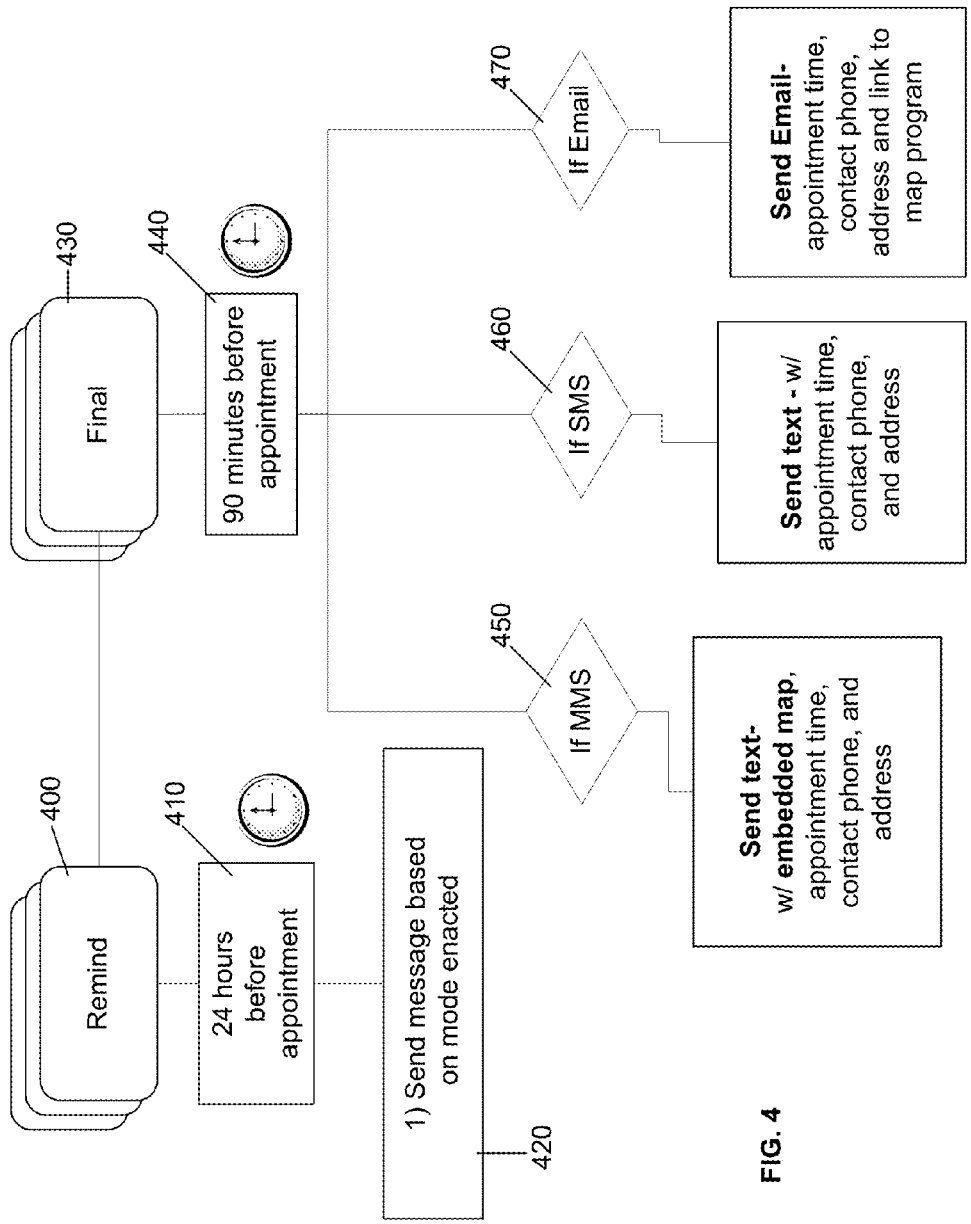

As shown in FIG. 4, in some implementations, the system may send a reminder message 400 at a predetermined time interval 410 prior to the appointment time based on the message mode enabled 420 by the stored information as to which format may be received by the patient's mobile device. An additional message 430 may also be sent at a time interval 440 that is after the reminder message is sent but before the appointment time. This additional message may contain additional information relating to the appointment. For example, if the additional message is in MMS format 450, the additional information may comprise text with an embedded map, appointment time, contact phone number, photo of the building, and address, etc. If the additional message is in SMS format 460, the additional information may comprise, by non-limiting example, text with the appointment time, contact phone number, and address, etc. Additionally, if the additional message is in email format 470, the email may include information such as, but not limited to, the appointment time, contact phone number, address, and a link to a web-based mapping program for mapping the appointment location, etc. One of ordinary skill in the art will recognize that static images, video, sound, and text may be embedded in MMS and other messaging formats and thus, patient communications may contain information relating to new services, display physician credentials, provide a direct video message from the office, provide notice of patient type that may benefit from specific treatment (e.g. flu shots, etc.) while remaining in compliance with HIPAA.

In some implementations, after an appointment is set, the system initiates an automated voice phone call to the patient. If answered, the system requests appointment confirmation by voice activation or by pressing a number on the keypad 160. If there is no answer or if voicemail is reached, the system waits for a predetermined period of time before reattempting confirmation. This sequence may occur multiple times. If after a predetermined number of attempts, a voicemail is reached, the system leaves a prerecorded or automated voice appointment reminder including information such as, but not limited to, patient name, date of appointment, and name of attending physician and recite a request for the patient to call the health care provider to confirm the appointment. One or more reminder automated voice phone calls may then be made at predetermined time intervals prior to the appointment to remind the patient of the upcoming appointment.

In some implementations, after an appointment is set, the system sends an initial appointment confirmation email message to the patient's email address requesting that the patient respond to the email to confirm the appointment 170. If no email response is received after a predetermined period of time, an additional confirmation request is emailed to the patient. This process may be repeated until a confirmation response is received from the patient. Reminder emails may be sent at predetermined time intervals prior to the appointment time. In some aspects, if no response is received to the reminder emails after a predetermined number of contact attempts, an exception report may be generated and supplied to the office. These reminder emails may also contain additional information such as a map of the office location or an embedded direct dial number to reach the health care provider.

In some implementations, the system further provides a "no-show revenue recovery" service that logs the time, date, computer, phone, or other relevant information to provide proof that the user had been notified or reminded of the appointment with ample time to comply with the health care provider's time frame requirements for appointment cancellation without the payment of a penalty fee, thereby reducing or eliminating disputes between patients and health care providers about whether a late cancellation fee is owed by the patient.

One of ordinary skill in the art would recognize that messages sent by the system to the mobile phone device may include navigational maps, written directions and other contact information. Messages may also include images, audio or video content without requiring an Internet access plan be provided by the wireless carrier because the content may be delivered directly to the wireless mobile device rather than through email or a web application that must be accessed on the device in order to view the content.

Additionally, the system may also include notification of laboratory testing results, general information regarding a medical office or practice such as, but not limited to new staff, hours, locations, billing reminders, immunization reminders, medication schedule reminders, prescription refill reminders, items to bring to visit reminders, or patient surveys.

The system may also be easily modified or adapted to operate in any situation, industry, or line of business where a combination of notification, messaging, or alerts is desired, such as by nonlimiting example, a dry cleaner, clothing or other retail store, optical store, automotive repair shop, or any other instance where an item is available for user pickup. The system may also be used in the insurance industry to provide notification and alerts regarding policy changes, updates, payment due dates, or other pertinent information. Surgical or laboratory testing centers may utilize the system to provide informational updates or instructions to patients for pre- and post-visit patient activities. The system may also be used to provide general disaster notification to alert message recipients as to steps to be taken prior to or after the occurrence of a regional disaster. Stores offering additional services beyond pharmacy, optical, or audiology may use reminders and alerts to provide information to users about related or other promotions that may be of interest to the user.

The system may also be utilized for the purpose of keeping in touch with a group of users by providing messages, reminders, and alerts, such as but not limited to churches and religious organizations, home owners' associations, social clubs, country clubs, athletic clubs, volunteer groups, civic groups, lobbying efforts, multi-level marketing organizations, or for automation of collection processes by collection agencies. The system may also be expanded to provide advertising or information on sponsors in conjunction with the messages that are sent to users.

It will be understood that implementations are not limited to the specific components disclosed herein, as virtually any components consistent with the intended operation of a method and/or system implementation for automated remote appointment confirmations, alerts, and reminders may be utilized.

In places where the description above refers to particular implementations of automated remote appointment confirmations, alerts, and reminders, it should be readily apparent that a number of modifications may be made without departing from the spirit thereof and that these implementations may be applied to other remote appointment confirmations, alerts, and reminders systems and methods. The presently disclosed implementations are, therefore, to be considered in all respects as illustrative and not restrictive.

The invention claimed is:

1. A computerized appointment confirmation system for communication with a mobile device comprising:
   a database comprising data regarding one or more appointments; and
   a server configured to:
      communicate with an MMS server upon creation of an appointment, the MMS server configured to send an MMS message to the mobile device and receive an MMS response message from the mobile device;
      receive a communication from the MMS server indicating receipt of the MMS response message by the MMS server;
      communicate with an SMS server when no MMS response message is received from the mobile device within a predetermined time period, the SMS server configured to send an SMS message to the mobile device and receive an SMS response message from the mobile device;
      update the database to indicate whether confirmation data was received by the MMS or SMS server from the mobile device;
      store in the database data indicating whether an MMS message or SMS message was received by the mobile device; and
      send a message to the mobile device at a predetermined time prior to the time at which the appointment is scheduled, the message being sent using MMS after having received a prior MMS response message from the mobile device, the sent message having additional information relating to the appointment comprising the appointment time, provider contact information, provider address, and an embedded map of a location of the appointment;
      wherein the server is further configured to poll at least one MMS server at a predetermined time interval for verification of online statue of the at least one MMS server, or poll at least one SMS server at a predetermined time interval for verification of online status of the at least one SMS server.

2. The system of claim 1, wherein the MMS message comprises identifying information that is retained in an SMS response message sent by the mobile device and received by the SMS server.

3. The system of claim 2, wherein the server is further configured to update the database in response to receipt of the SMS response message by the SMS server to indicate that an MMS message was received by the mobile device.

4. The system of claim 1, wherein the server is further configured to:
   send an email message to the mobile device if an MMS or SMS response message is not received by the MMS or SMS servers within a predetermined time period; and
   store in the database data indicating receipt of an email response message when an email response message is received from the mobile device.

5. The system of claim 1, wherein the server is further configured to:
   communicate with the MMS server wherein the MMS server sends a second MMS message to the mobile device when an SMS response is not received by the SMS server within a predetermined time period.

6. The system of claim 1, wherein the server is further configured to receive an error message from the SMS server and generate an exception report.

7. The system of claim 1, wherein the server is further configured to send a reminder message to the mobile device at a predetermined time prior to the time at which the appointment is scheduled, the reminder message being sent using the same communication method as that which resulted in a prior response message from the mobile device.

8. The system of claim 1, wherein the communication method is SMS and the additional information comprises the appointment time, provider contact information, and provider address.

9. The system of claim 1, wherein the communication method is email and the additional information comprises the appointment time, provider contact information, provider address, and web link to an online map of the provider's location.

10. A computerized appointment confirmation method for communication with a mobile device, the method comprising:
    storing in a database, using a server, data regarding one or more appointments;
    communicating, by the server, with an MMS server upon creation of an appointment, the MMS server configured to send an MMS message to the mobile device and receive an MMS response message from the mobile device;
    receiving, by the server, a communication from the MMS server indicating receipt of the MMS response message by the MMS server;
    communicating, by the server, with an SMS server when no MMS response message is received from the mobile device within a predetermined time period, the SMS server configured to send an SMS message to the mobile device and receive an SMS response message from the mobile device;
    updating the database, by the server, to indicate whether confirmation data was received by the MMS or SMS server from the mobile device;
    storing in the database, data indicating whether an MMS message or SMS message was received by the mobile device;
    sending a message to the mobile device at a predetermined time prior to the time at which the appointment is scheduled, the message being sent using MMS after having received a prior MMS response message from the mobile device, the sent message having additional information relating to the appointment comprising the appointment time, provider contact information, provider address, and an embedded map of a location of the appointment; and
    polling at least one MMS server or at least one SMS server at a predetermined time interval for verification of online status of the at least one MMS server or for verification of online status of the at least one SMS server.

11. The method of claim 10 wherein the MMS message comprises identifying information that is retained in an SMS response message sent by the mobile device and received by the SMS server.

12. The method of claim 11 further comprising updating the database in response to receipt of the SMS response message by the SMS server to indicate that an MMS message was received by the mobile device.

13. The method of claim 10, further comprising:
    sending, by the server, an email message to the mobile device if an MMS or SMS response message is not received by the MMS or SMS servers within a predetermined time period; and
    storing in the database, by the server, data indicating receipt of an email response message when an email response message is received from the mobile device.

14. The method of claim 10, further comprising:
    communicating, by the server, with the MMS server wherein the MMS server sends a second MMS message to the mobile device when an SMS response is not received by the SMS server within a predetermined time period.

15. The method of claim 14, wherein the communication method is SMS and the additional information comprises the appointment time, provider contact information, and provider address.

16. The method of claim 10, further comprising:
    receiving, by the server, an error message from the SMS server and generating an exception report.

17. The method of claim 10, further comprising:
    sending, by the server, a reminder message to the mobile device at a predetermined time prior to the time at which the appointment is scheduled, the reminder message being sent using the same communication method as that which resulted in a prior response message from the mobile device.

18. The method of claim 10, wherein the communication method is email and the additional information comprises the appointment time, provider contact information, provider address, and web link to an online map of the provider's location.

19. A non-transitory computer readable medium for computerized appointment confirmation utilizing communication with a mobile device, the computer readable medium having program code stored therein that when executed is configured to:
    store in a database, using a server, data regarding one or more appointments;
    communicate, by the server, with an MMS server upon creation of an appointment, the MMS server configured to send an MMS message to the mobile device and receive an MMS response message from the mobile device;
    receive, by the server, a communication from the MMS server indicating receipt of the MMS response message by the MMS server;
    communicate, by the server, with an SMS server when no MMS response message is received from the mobile device within a predetermined time period, the SMS server configured to send an SMS message to the mobile device and receive an SMS response message from the mobile device;

update the database, by the server, to indicate whether confirmation data was received by the MMS or SMS server from the mobile device;

store in the database, data indicating whether an MMS message or SMS message was received by the mobile device;

send a message to the mobile device at a predetermined time prior to the time at which the appointment is scheduled, the message being sent using MMS after having received a prior MMS response message from the mobile device, the sent message having additional information relating to the appointment comprising the appointment time, provider contact information, provider address, and an embedded map of a location of the appointment; and poll at least one MMS server or at least one SMS server at a predetermined time interval for verification of online status of the at least one MMS server or for verification of online status of the at least one SMS server.

20. The non-transitory computer readable medium of claim 19, wherein the MMS message comprises identifying information that is retained in an SMS response message sent by the mobile device and received by the SMS server.

21. The non-transitory computer readable medium of claim 20, further configured to update the database in response to receipt of the SMS response message by the SMS server to indicate that an MMS message was received by the mobile device.

22. The non-transitory computer readable medium of claim 19, further configured to:

send, by the server, an email message to the mobile device if an MMS or SMS response message is not received by the MMS or SMS servers within a predetermined time period; and store in the database, by the server, data indicating receipt of an email response message when an email response message is received from the mobile device.

23. The non-transitory computer readable medium of claim 19, further configured to:

communicate, by the server, with the MMS server wherein the MMS server sends a second MMS message to the mobile device when an SMS response is not received by the SMS server within a predetermined time period.

24. The computer readable medium of claim 19, further configured to:

receive, by the server, an error message from the SMS server and generating an exception report.

25. The non-transitory computer readable medium of claim 19, further configured to:

send, by the server, a reminder message to the mobile device at a predetermined time prior to the time at which the appointment is scheduled, the reminder message being sent using the same communication method as that which resulted in a prior response message from the mobile device.

26. The non-transitory computer readable medium of claim 19, wherein the communication method is SMS and the additional information comprises the appointment time, provider contact information, and provider address.

27. The non-transitory computer readable medium of claim 19, wherein the communication method is email and the additional information comprises the appointment time, provider contact information, provider address, and web link to an online map of the provider's location.

* * * * *